United States Patent [19]
Choudary et al.

[11] Patent Number: 6,034,287

[45] Date of Patent: Mar. 7, 2000

[54] PROCESS FOR THE PRODUCTION OF NITROARENES WITH HIGH PARA-SELECTIVITY FROM MONOSUBSTITUTED AROMATIC HYDROCARBONS USING ALUMINO-SILICATES AS CATALYSTS

[75] Inventors: Boyapati Manoranjan Choudary; Mutyala Sateesh; Mannepalli Lakshmi Kantam; Kottapalli Koteswara Rao; Kompella Vishweshwar Ram Prasad; Kondapuram Vijaya Raghavan, all of Hyderabad, India

[73] Assignee: Coucil of Scientific and Industrial Research, New Delhi, India

[21] Appl. No.: 09/188,589

[22] Filed: Nov. 9, 1998

[30] Foreign Application Priority Data

Sep. 25, 1998 [IN] India ............................. 2874/DEL/98

[51] Int. Cl.[7] ................................................ C07C 205/00
[52] U.S. Cl. ............................................................ 568/927
[58] Field of Search .............................................. 568/927

[56] References Cited

U.S. PATENT DOCUMENTS 5,004,846 4/1991 Sato et al. ................................ 568/940

OTHER PUBLICATIONS

Jounal of Organic Chemistry 1994, 59, 4939–4942.

Primary Examiner—Paul J. Killos
Assistant Examiner—J. Parsa
Attorney, Agent, or Firm—Ladas & Parry

[57] ABSTRACT

The present invention relates to a process for the production of nitroarenes with high para-selectivity from monosubstituted aromatic hydrocarbons using aluminosilicates as catalysts, which comprises nitration of monosubstituted aromatic hydrocarbons using aluminosilicates of different ratios wherein Si/Al ranges between 5 to 1000 and the said aluminosilicates being manifested in the form of variety of zeolites and K10 montmorillonite as catalysts using nitric acid in the molar ratio of nitric acid to monosubstituted aromatic hydrocarbons ranging between 0.25 to 2.5 at a temperature in the range of 30–160° C. for a period ranging between 0.25 to 3.0 h and followed by continuous removal of water formed from the reaction mixture with a Dean-Stark apparatus and recovery of the product mixture by concentration of the reaction mixture after separation of the catalyst by filtration.

14 Claims, No Drawings

PROCESS FOR THE PRODUCTION OF NITROARENES WITH HIGH PARA-SELECTIVITY FROM MONOSUBSTITUTED AROMATIC HYDROCARBONS USING ALUMINO-SILICATES AS CATALYSTS

FIELD AND PREFERRED FEATURES OF THE INVENTION

The present invention relates to a process for the production of nitroarenes with high para-selectivity from monosubstituted aromatic hydrocarbons using aluminosilicates as catalysts.

This invention particularly relates to a process for nitration of monosubstituted aromatic hydrocarbons using aluminosilicate catalysts as solid acids dispensing with the use of $H_2SO_4$ which totally eliminates disposal of salts formed consequent to the neutralisation of sulfuric acid. The production of p-nitroaromatics with enhanced selectivity over the o-nitroproducts which is described here is prompted by market driven research, since the p-isomers are in greater demand.

This invention particularly relates to an improved selectivity of p-isomers over o-isomers offers simplification of the process for the separation of isomers.

This invention particularly relates to an improved ecofriendly process, which minimises effluents, requires very small amount of water for washings and is non-corrosive in nature, in contrast to the process practiced currently in industry with sulfuric acid.

This invention particularly relates to an improved and cost effective process with enhanced selectivity of p-isomers over conventional sulfuric acid process currently under practice in industry, employing small amount of catalyst with reusability demonstrated for number of cycles.

BACKGROUND AND PRIOR ART REFERENCES OF THE INVENTION

Nitration process is used for the production of many large-volume chemicals such as nitrotoluenes, nitrochlorobenzenes and other nitroarenes which are vital intermediates for dyes, pharmaceuticals, perfumes and pesticides. Nitration of arenes is performed classically with a mixture of nitric and sulfuric acids. Major disadvantages of this method are formation of by-products of polynitration and environmental pollution during disposal of spent acid.

Reference may be made to a US patent (U.S. Pat. No. 4,418,230 November 1983) wherein a method for nitration of toluene with $HNO_3$ and $H_2SO_4$ at 0–50° C. is described (o:m:p 55:2.3:38.9). The drawbacks are the use of sulfuric acid and also the formation of more of o-isomer.

Reference may be made to another US patent (U.S. Pat. No. 1,12,006 September 5) wherein a process for nitration of toluene with $HNO_3$ and 10% $H_2SO_4$ impregnated $Al_2O_3$ and 1% Mo at 135–145° C./20 Torr is described (o:m:p 34.0:3.5:62.5). The drawbacks are using of sulfuric acid in the preparation of the catalyst and the catalyst gets deactivated on each cycle.

Although it has been known for some time that benzene and its homologs can be nitrated with $HNO_3$ alone without using sulfuric acid, little or no progress has been made in this direction on commercial scale. The disadvantage in this method is the low productivity and the use of large excess of nitric acid (molar ratio of nitric acid to benzene is 2:1 to 4:1) which increase the possibility of poly-nitro compounds formation and affect the economics of the project. Recently attention has been focused on the development of environmentally friendly solid acid catalysts such as Nafion especially in Friedel-Crafts reactions to replace environmentally hazardous sulfuric acid in nitration reactions.

Reference may be made to a US patent (U.S. Pat. No. 4,234,470; Nov. 18, 1980) wherein a method for nitration of benzene, chlorobenzene and toluene with $HNO_3$ in presence of Nafion catalyst is described. The drawbacks are the use of expensive Nafion resin whose activity is decreasing on each cycle and offers nearly identical isomeric selectivity (o:m:p 56:4:40) as that of mixed acid.

Reference may also be made to a Japanese patent (Jpn. Kokai Tokkyo Koho JP 63, 303, 957, June, 1987) wherein a process for vapour phase nitration of halobenzenes with $HNO_3$ and aluminosilicates at 175° C. and space velocity 2.2 $h^{-1}$ (nitration of chlorobenzene isomeric ratio: o:m:p 14.5:1.7:83.8) is described. The draw backs are that the reactions are carried in vapour phase conditions. Reference may also be made to an Indian patent (Appl., NS90/97 2937 Del 97 October 1997) and an European patent (Appl., 98302258. 3-1521, Mar. 25, 1998) wherein a process for the production of nitroarenes from arenes with fuming $HNO_3$ in presence of exchanged clays as catalysts is described. The draw backs are that this invention does not significantly alter isomeric composition of disubstituted benzenes.

Reference may also be made to a publication (Chem.Commun, 469, 1996) wherein benzene, alkylbenzenes and halobenzenes are nitrated in quantitative yields and with high para-selectivity in a solvent free process by use of a stoichiometric quantity of nitric acid and acetic anhydride at 0–20° C. in the presence of zeolite beta as a recyclable catalyst. Reference may be also made to a publication (Catal.Lett., 255, 1997) wherein halobenzenes are nitrated in quantitative yields and with high para-selectivity in $CCl_4$ solvent by using stoichiometric quantities of nitric acid and acetic anhydride at room temperature and 70° C. in the presence of sulphated zirconica ($SO_4^{2-}/ZrO_2$) as catalyst. Reference may also be made to publication (J. Mol. Catal., 87, 33, 1994) wherein halobenzenes are nitrated in good yields and with high para-selectivity in $CCl_4$ solvent by use of a stoichiometric quantity of nitric acid and acetic anhydride at room temperature to 80° C. in the presence of $Fe^{3+}$-montmorillonite catalyst. The draw backs are the use of expensive acetic anhydride in all the above processes which is uneconomical and also exothermic and explosive nature of the reaction of acetic anhydride and nitric acid.

Reference may also be made to a publication (Chem. Commun., 613, 1997) wherein aromatics are nitrated in good yields in dichloroethane solvent by using stoichiometric quantities of 69% nitric acid at reflux temperature of solvent in the presence of lanthanide(III) triflates as recyclable catalysts. The draw backs are the slowness of the reaction which takes more time for completion of the reaction, the use of expensive catalyst and the process will be of low productivity. The isomeric ratio is also identical with that of mixed acids.

The main objective of the present invention is to provide a process for the production of nitroarenes with high para-selectivity from monosubstituted aromatic hydrocarbons using aluminosilicates as catalysts which obviates the drawbacks as detailed above. Another object of the present invention is the use of ecofriendly modified aluminosilicates as solid acid catalysts in the nitration of monosubstituted arenes dispensing the use of sulfuric acid which obviates the drawbacks as detailed above.

Yet another object of the present invention is to dispense with the use of acetic anhydride which obviates the drawbacks as detailed above.

DETAILED DESCRIPTION OF THE INVENTION

Accordingly the present invention provides a process for the production of nitroarenes with high para-selectivity from monosubstituted aromatic hydrocarbons using aluminosilicates as catalysts which comprises nitration of monosubstituted aromatic hydrocarbons using aluminosilicates of different ratios (Si/Al=5 to 1000) manifested in the form of variety of zeolites and K10 montmorillonite as catalysts using nitric acid in the molar ratio of nitric acid to monosubstituted benzenes 0.25 to 2.5 in the range of 30–160° C. for 0.25 to 3.0 h and continuous removal of water formed from the reaction mixture with a Dean-Stark apparatus and recovery of the product mixture by concentration of the reaction mixture after separation of the catalyst by filtration.

In an embodiment of the present invention, the catalysts used are aluminosilicates.

In another embodiment of the present invention Si/Al ratio varies from 5 to 1000 in the synthesis of various aluminosilicates. The type of zeolite and Si/Al ratio is critical in achieving high para-selectivity.

In yet another embodiment of the present invention nitric acid was used as the nitrating agent and the molar ratio of nitric acid to aromatics should normally be in the range from 0.5 to 2.5.

In still another embodiment of the present invention, nitric acid was used as the nitrating agent and the scale of the reaction conducted ranges from 4000 mmol to 10 mmol per batch.

In still another embodiment of the present invention, nitric acid was used as the nitrating agent should normally be in the concentration range from 50 to 90% (w/v) desirably 60 to 70%.

In still another embodiment of the present invention monosubstituted benzenes used are selected from toluene, ethylbenzene, cumene, anisole, chlorobenzene, bromobenzene and iodobenzene.

In still another embodiment of the present invention, the catalysts used are aluminosilicates selected from zeolite beta, K-10 montmorillonite, ZSM-5, Mordenite, TS-1 and HY zeolite.

In still another embodiment of the present invention, zeolite Beta is preferred as the catalyst used with Si/Al ratio ranging between 15–22 to obtain high para selectivity.

In still another embodiment of the present invention, nitration is effected at a temperature in the range of 30 to 160° C.

In still another embodiment of the present invention reaction time of nitration is effected in between 0.25 to 3.0 h.

In still another embodiment of the present invention, the product ratio for ortho:meta:para ranges from 29.4:2.3:65.7 to 5.4:6.5:36.4 depending upon the catalyst used.

In still another embodiment of the present invention, the product ratio for ortho:meta:para ranges from 13:0:87 to 25:0:73 depending upon the substrate used.

In still another embodiment of the present invention the selectivity of the para-isomer increases with the increase of catalyst amount (for example p-nitrotoluene increases to 72–75%).

In still another embodiment of the present invention, selectivity of p-isomer increases to the extent of 5–10% with the increase of catalyst amount.

In still another embodiment of the present invention the use of aluminosilicates as solid catalysts dispenses the use of hazardous sulfuric acid.

In still another embodiment of the present invention the catalyst not only imparts high activity by the presence of acidic sites and high para-selectivity due to the restricted dimensional configuration of the catalysts.

In still another embodiment of the present invention the solid acid catalysts used here act as bifunctional catalysts, generating electrophile, nitronium ion as well as instant adsorbent for water formed during the reaction to facilitate electrophilic substitution on arenes.

In still another embodiment of the present invention nitration is effected by continuous azeotropical removal of water present in the nitric acid and formed during the reaction with a Dean-Stark apparatus using the substrate as self solvent or chlorohydrocarbons as solvent to regenerate active sites of the catalyst generating nitronium ions.

In still another embodiment of the present invention recovery of nitroarenes is carried out by separating the catalyst by filtration and removing the excess of unreacted arenes by distillation or by concentration in rotavapor.

Monosubstituted benzenes and the catalyst were taken in a two-necked round-bottomed flask equipped with Dean-Stark apparatus. After the flask was heated to the required temperature, nitric acid was added dropwise into the reaction mixture over the required period. Simultaneously, the water collected in the the Dean-Stark apparatus formed from the reaction was removed continuously. After completion of the reaction, the catalyst was filtered and the reaction mixture was concentrated to obtain the mixture of nitrotoluenes. The monosubstituted benzenes used are selected from monosubstituted aromatics, preferably from toluene, anisole, ethylbenzene, cumene, chlorobenzene, bromobenzene and iodobenzene and the amount used ranges from 4000 to 10 mmol. The molar ratio of nitric acid and aromatic should normally be in the range from 0.25 to 2.5, desirably 0.5 to 2.0. Nitration reaction temperature should normally be in the range from 30 to 190° C., desirably from 80 to 160° C. Nitration process was accomplished in a period of 0.25 to 5.0 h, preferably about 0.5 to 3.0 h.

The principal object of the present invention by processing under the above conditions, therefore, was to produce cost effective predominantly para-selective product over the previously reported works. It was achieved because of the possible restricted pore sizes of the aluminosilicates used as solid acid catalysts and also the methodology used in this process. The other object of the present invention was achieved by using the aluminosilicates as solid acid catalysts replacing the hazardous sulfuric acid.

The novelty of the present invention with respect to the prior art is to produce predominantly p-isomer in the nitration of aromatic hydrocarbons using solid acids as catalysts replacing liquid sulfuric acid employed in more than stoichiometric quantities. The selectivity is possible by the use of solid acids of compatible pore dimensions designed and modified to direct the electrophile, nitronium ion to substitute at the para-position in preference to ortho-position. Apart from generating nitronium ion by the aluminosilicate catalyst, the process is engineered to drive away water formed in the reaction as well as present in the nitric acid by azeotropic distillation enables the easy access of acidic sites of solid catalysts for recycle and available in constant number resulting in high productivity with good p-selectivity.

The following examples are given by way of illustration of the present invention and therefore should not be construed to limit the scope of the present invention.

EXAMPLE 1

Aluminosilicates: A series of catalysts prepared or sourced from commercial samples were used.

Zeolite beta: (Tetraethyl orthosilicate and aluminium nitrate of appropriate molar ratios to get desired ratio of Si/Al ranging from 5 to 100 were used). Water is added to tetraethylortho silicate and stirred. To this solution aluminium nitrate, nonahydrate in tetraethylammonium hydroxide solution is added dropwise by a pressure regulating funnel under stirring. After the addition, the solution is kept at 50° C. for one day and at 135° C. in an autoclave for one week for crystallization. Then filtered the solid and air dried.

ZSM-5: ZSM-5 obtained from Zeolyst International was used as such.

Mordenite: Mordenite, obtained from Zeolyst International was used as such.

TS-1: TS-1 obtained from IRC, Lyon, France was used as such.

HY: $NH_4Y$ obtained from Zeolyst International was calcined at 500° C. to obtain HY.

K10 montmorillonite: Montmorillonite employed in the synthesis was obtained from Fluka Grade (K10) with exchange capacity of 0.8 m eq./g.

EXAMPLE 2

Toluene 10 ml (94.1 mmol) and zeolite beta catalyst (0.5 g) were taken in a 50 ml two-necked round-bottomed flask equipped with Dean-Stark apparatus. The mixture was heated to reflux temperature and 60% nitric acid 5 ml (63 mmol) was added dropwise into the reaction mixture over a period of ½ h. Simultaneously, the water collected in the the Dean-Stark apparatus formed from the reaction was removed continuously. After completion of the reaction, the catalyst was filtered and the reaction mixture was concentrated to obtain the mixture of nitrotoluenes.

Yiled: 4.7 g

EXAMPLE 3

A mixture of toluene 10 ml (94.1 mmol) and K10-montmorillonite catalyst (0.5 g) were taken in a 50 ml two-necked round-bottomed flask equipped with Dean-Stark apparatus. The mixture was heated to reflux temperature and 60% nitric acid 5 ml (63 mmol) was added dropwise into the reaction mixture over a period of ½ h where upon the liberated water collected in the Dean-Stark apparatus was removed continuously. After completion of the reaction, the catalyst was filtered and the reaction mixture was concentrated to obtain the mixture of nitrotoluenes.

Yield: 4.5 g

EXAMPLE 4

A mixture of toluene 10 ml (94.1 mmol) and ZSM-5 catalyst (0.5 g) were taken in a 50 ml two-necked round-bottomed flask equipped with Dean-Stark apparatus. The mixture was heated to reflux temperature and 60% nitric acid 5 ml (63 mmol) was added dropwise into the reaction mixture over a period of ½ h where upon the liberated water collected in the Dean-Stark apparatus was removed continuously. After completion of the reaction, the catalyst was filtered and the reaction mixture was concentrated to obtain the mixture of nitrotoluenes.

Yield: 2.8 g

EXAMPLE 5

A mixture of toluene 10 ml (94.1 mmol) and mordenite catalyst (0.5 g) were taken in a 50 ml two-necked round-bottomed flask equipped with Dean-Stark apparatus. The mixture was heated to reflux temperature and 60% nitric acid 5 ml (63 mmol) was added dropwise into the reaction mixture over a period of ½ h where upon the liberated water collected in the Dean-Stark apparatus was removed continuously. After completion of the reaction, the catalyst was filtered and the reaction mixture was concentrated to obtain the mixture of nitrotoluenes.

Yield: 4.7 g

EXAMPLE 6

A mixture of toluene 10 ml (94.1 mmol) and TS-1 catalyst (0.5 g) were taken in a 50 ml two-necked round-bottomed flask equipped with Dean-Stark apparatus. The mixture was heated to reflux temperature and 60% nitric acid 5 ml (63 mmol) was added dropwise into the reaction mixture over a period of ½ h where upon the liberated water collected in the Dean-Stark apparatus was removed continuously. After completion of the reaction, the catalyst was filtered and the reaction mixture was concentrated to obtain the mixture of nitrotoluenes.

Yield: 4.7 g

EXAMPLE 7

A mixture of toluene 10 ml (94.1 mmol) and HY catalyst (0.5 g) were taken in a 50 ml two-necked round-bottomed flask equipped with Dean-Stark apparatus. The mixture was heated to reflux temperature and 60% nitric acid 5 ml (63 mmol) was added dropwise into the reaction mixture over a period of ½ h where upon the liberated water collected in the Dean-Stark apparatus was removed continuously. After completion of the reaction, the catalyst was filtered and the reaction mixture was concentrated to obtain the mixture of nitrotoluenes.

Yield: 2.7 g

EXAMPLES 8

A mixture of toluene 170 ml (1600 mmol) and fresh zeolite beta catalyst (10 g) were taken in a 1000 ml reactor flask equipped with Dean-Stark apparatus. The mixture was heated to reflux temperature and 60% nitric acid 120 ml (1512 mmol) was added dropwise with infusion pump over a period of 1 h 35 min into the reaction mixture where upon the liberated water collected in the Dean-Stark apparatus was continuously removed. After completion of the reaction, the catalyst was filtered and the reaction mixture was concentrated to obtain the mixture of nitrotoluenes.

Yield: 105.6 g

A sample drawn at a half an hour interval showed the para-selectivity to the extent of 75% which is 10% more than the isomeric ratio obtained at the end of the reaction.

EXAMPLES 9–13

A mixture of toluene 170 ml (1600 mmol) and used zeolite beta catalyst (10 g) (1st recycle to 5th recycle) were taken in a 1000 ml reactor flask equipped with Dean-Stark apparatus. The mixture was heated to reflux temperature and 60% nitric acid 120 ml (1512 mmol) was added dropwise with infusion pump over a period of 1 h 35 min into the reaction mixture where upon the liberated water collected in the Dean-Stark apparatus was continuously removed. After completion of the reaction, the catalyst was filtered and the reaction mixture was concentrated to obtain the mixture of nitrotoluenes.

EXAMPLE 14

A mixture of chlorobenzene 8.6 ml (76.6 mmol) and zeolite beta catalyst (1 g) were taken in a 50 ml two-necked round-bottomed flask equipped with Dean-Stark apparatus. The mixture was heated to reflux temperature and conc. nitric acid (5 ml, 76.6 mmol) was added dropwise over a period of ½ h into the reaction mixture where upon the liberated water collected in the Dean-Stark apparatus was continuously removed. After completion of the reaction, catalyst was filtered and the reaction mixture was concentrated to obtain the mixture of nitrochlorobenzenes.

Yield: 6.2 g

EXAMPLE 15

A mixture of chlorobenzene 8.6 ml (76.6 mmol) and zeolite beta catalyst (1 g) were taken in a 50 ml two-necked round-bottomed flask equipped with Dean-Stark apparatus. The mixture was heated to reflux temperature and conc. nitric acid (10 ml, 153.2 mmol) was added dropwise over a period of 1 h into the reaction mixture where upon the liberated water collected in the Dean-Stark apparatus was continuously removed. After completion of the reaction, catalyst was filtered and the reaction mixture was concentrated to obtain the mixture of nitrochlorobenzenes.

Yield: 11.8 g

EXAMPLE 16

A mixture of bromobenzene 8.0 ml (76.6 mmol), zeolite beta catalyst (1 g) and dichloroethane (10 ml) were stirred in a 50 ml two-necked round bottomed flask. The mixture was heated to reflux temperature and conc. nitric acid 5 ml (76.6 mmol) was added dropwise over a period of ½ h into the reaction mixture where upon the liberated water collected in the Dean-Stark apparatus was continuously removed. After completion of the reaction, catalyst was filtered and the reaction mixture was concentrated to obtain the mixture of nitrobromobenzenes.

Yield: 7.9 g

EXAMPLE 17

A mixture of bromobenzene 8.0 ml (76.6 mmol), zeolite beta catalyst (1 g) and dichloroethane 10 ml were stirred in a 50 ml two-necked round bottomed flask. The mixture was heated to reflux temperature and conc. nitric acid 10 ml (153.2 mmol) was added dropwise over a period of 1 h into the reaction mixture where upon the liberated water collected in the Dean-Stark apparatus was continuously removed. After completion of the reaction, catalyst was filtered and the reaction mixture was concentrated to obtain the mixture of nitrobromobenzenes.

Yield: 9.9 g

EXAMPLE 18

A mixture of iodobenzene 8.5 ml (76.6 mmol), zeolite beta catalyst (1 g) and dichloroethane 10 ml were taken in a 50 ml two-necked round bottomed flask equipped with a Dean-Stark apparatus. The mixture was heated to reflux temperature and conc. nitric acid 5 ml (76.6 mmol) was added dropwise over a period of ½ h into the reaction mixture where upon the liberated water collected in the Dean-Stark apparatus was continuously removed. After completion of the reaction, catalyst was filtered and the reaction mixture was concentrated to obtain the mixture of nitroiodobenzenes.

Yield: 9.9 g

EXAMPLE 19

A mixture of ethylbenzene 9.4 ml (76.6 mmol) and zeolite beta catalyst (1 g) were taken in a 50 ml two-necked round-bottomed flask equipped with Dean-Stark apparatus. The mixture was heated to reflux temperature and conc. nitric acid 5 ml (76.6 mmol) was added dropwise over a period of ½ h into the reaction mixture where upon the liberated water collected in the Dean-Stark apparatus was continuously removed. After completion of the reaction, catalyst was filtered and the reaction mixture was concentrated to obtain the mixture of nitroethylbenzenes.

Yield: 5.51 g

EXAMPLE 20

A mixture of ethylbenzene 9.4 ml (76.6 mmol) and zeolite beta catalyst (1 g) were taken in a 50 ml two-necked round-bottomed flask equipped with Dean-Stark apparatus. The mixture was heated to reflux temperature and conc. nitric acid 10 ml (153.2 mmol) was added dropwise over a period of 1 h into the reaction mixture where upon the liberated water collected in the Dean-Stark apparatus was continuously removed. After completion of the reaction, catalyst was filtered and the reaction mixture was concentrated to obtain the mixture of nitroethylbenzenes.

Yield: 10.9 g

EXAMPLE 21

A mixture of cumene 10.6 ml (76.6 mmol), zeolite beta catalyst(1 g) and dichloroethane 10 ml were taken in a 50 ml two-necked round bottomed flask equipped with a Dean-Stark apparatus. The mixture was heated to reflux temperature and conc. nitric acid 5 ml (76.6 mmol) was added dropwise over a period of ½ h into the reaction mixture where upon the liberated water collected in the Dean-Stark apparatus was continuously removed. After completion of the reaction, catalyst was filtered and the reaction mixture was concentrated to obtain the mixture of nitrocumenes.

Yiled: 6.4 g

EXAMPLE 22

A mixture of anisole 8.3 ml (76.6 mmol) and zeolite beta catalyst (1 g) were taken in a 50 ml two-necked round-bottomed flask equipped with Dean-Stark apparatus. The mixture was heated to reflux temperature and conc. nitric acid 5 ml (76.6 mmol) was added dropwise over a period of ½ h into the reaction mixture where upon the liberated water collected in the Dean-Stark apparatus was continuously removed. After completion of the reaction, catalyst was filtered and the reaction mixture was concentrated to obtain the mixture of nitroanisoles.

Yield: 5.7 g

EXAMPLE 23

A mixture of anisole 8.3 ml (76.6 mmol) and zeolite beta catalyst (1 g) were taken in a 50 ml two-necked round-bottomed flask equipped with Dean-Stark apparatus. The mixture was heated to reflux temperature and conc. nitric acid 10 ml (153.2 mmol) was added dropwise over a period of 1 h into the reaction mixture where upon the liberated water collected in the Dean-Stark apparatus was continu ously removed. After completion of the reaction, catalyst was filtered and the reaction mixture was concentrated to obtain the mixture of nitroanisoles.

Yield: 11.2 g

TABLE 1

Nitration of toluene with various catalysts

| Example | Catalyst | Isolated Yield (%)[a] | product distribution | | | |
|---|---|---|---|---|---|---|
| | | | ortho | meta | para | others[b] |
| 2. | zeolite beta | 55.0 | 29.4 | 2.3 | 65.7 | 2.6 |
| 3. | K10-mont. | 52.5 | 44.1 | 3.2 | 50.0 | 3.0 |
| 4. | ZSM-5 | 32.0 | 47.0 | 6.4 | 43.0 | 2.9 |
| 5. | Mordenite | 35.2 | 54.0 | 6.5 | 36.4 | 2.9 |
| 6. | TS-1 | 55.0 | 51.8 | 5.8 | 35.5 | 7.0 |
| 7. | HY | 31.5 | 50.8 | 7.4 | 35.0 | 4.8 |

[a]The results are based on single pass of nitric acid, rest of the $HNO_3$ is distilled along with azeotrope during the reaction. The yields are higher than 95% in all experiments, when nitric acid consumed in the reaction is taken into account.
[b]2,4-Dinitrotoluene, 2,6-Dinitrotoluene, benzaldehyde and polymeric species.
It is found that zeolite beta is an effective catalyst for the production of nitroaromatic compounds with high para-selectivity.

TABLE 2

Catalyst reusability experiments in the nitration of toluene

| Example | Catalyst cycles | Product distribution | | | |
|---|---|---|---|---|---|
| | | ortho | meta | para | others[a] |
| 8. | zeolite beta | 33.2 | 1.6 | 63.6 | 1.4 |
| 9. | Ist recycle | 32.5 | 3.5 | 62.4 | 1.3 |
| 10. | IInd recycle | 29.8 | 2.6 | 65.6 | 1.8 |
| 11. | IIIrd recycle | 33.5 | 3.8 | 58.1 | 4.6 |
| 12. | IVth recycle | 34.6 | 3.8 | 58.9 | 2.7 |
| 13. | Vth recycle | 34.7 | 3.8 | 58.6 | 2.9 |

[a]2,4-Dinitrotoluene and 2,6-Dinitrotoluene are always less than 0.2% in all cases and the remaining products are benzaldehyde and polymeric species
It was found that zeolite beta is an effective catalyst for the production of nitroaromatic compounds with high para-selectivity and the catalyst can be used for several recycles.

TABLE 3

Nitration of monosubstituted aromatics

| Example | Aromatic | Temp °C. | Isolated Yield (%) | Product distribution | | | |
|---|---|---|---|---|---|---|---|
| | | | | ortho | meta | para | others[a] |
| 14. | Chlorobenzene | 140 | 51.4[b] | 13.0 | — | 87.0 | — |
| 15. | Chlorobenzene | 140 | 98.0[c] | 13.0 | — | 87.0 | — |
| 16. | Bromobenzene | 100 | 50.9[b] | 18.0 | — | 82.0 | — |
| 17. | Bromobenzene | 100 | 96.7[c] | 18.0 | — | 82.0 | — |
| 18. | Iodobenzene | 100 | 52.1 | 23.7 | — | 72.3 | — |
| 19. | Ethylbenzene | 140 | 47.4[b] | 6.9 | — | 47.3 | 45.8 |
| 20. | Ethylbenzene | 140 | 95.0[c] | 3.7 | — | 52.0 | 44.2 |
| 21. | Cumene | 100 | 51.4 | 18.5 | — | 78.0 | 3.5 |
| 22. | Anisole | 155 | 48.5[b] | 25.0 | — | 73.0 | 2.0 |
| 23 | Anisole | 155 | 96.0[c] | 24.8 | — | 72.5 | 2.7 |

[a]Oxidation products
[b]Aromatics and nitric acid ratio 1:1
[c]Aromatics and nitric acid ratio 1:2, yield based on arenes Nitro aromatic compounds were obtained with high para-selectivity using zeolite beta as the catalyst.

The main advantages of the present invention are:
1. A simplified method and an ecofriendly process for production of substituted nitroarenes was developed.
2. A simplified method for obtaining nitroarenes with high para-selectivity was developed.
3. The use of sulfuric acid, a hazardous chemical is dispensed with.
4. The use of an expensive acetic anhydride which forms an explosive mixture in conjunction with nitric acid in some of the methodologies is also dispensed with.
5. The present process envisages no disposable problem as the catalyst can be used for several recycles. The catalyst was subjected to 4 recycles which displayed almost consistent activity and selectivity.
6. Continuous removal of water from the reaction mixture and ease of separation of the catalysts by filtration after the process makes this process simple.
7. The present process is environmentally safe since there is no effluent disposable problem.

We claim:

1. A process for the production of nitroarenes with high para selectivity from monosubstituted aromatic hydrocarbons using aluminosilicates as catalysts, which comprises nitration of monosubstituted aromatic hydrocarbons using beta zeolite with Si/Al of from 15 to 22 as catalyst using nitric acid as nitrating agent with azeotropic removal of water formed and present in the reaction mixture.

2. A process as claimed in claim 1 wherein nitric acid was used as the nitrating agent and the molar ratio of nitric acid to aromatics ranging between 0.5 to 2.5.

3. A process as claimed in claim 1 wherein nitric acid was used as the nitrating agent in the concentration ranging from 60 to 70%.

4. A process as claimed in claim 1 wherein monosubstituted aromatic hydrocarbons used are selected from toluene, ethylbenzene, cumene, anisole, chlorobenzene, bromobenzene and Iodobenzene.

5. A process as claimed in claim 1 wherein nitration is effected at a temperature in the range of 30 to 160° C.

6. A process as clamed in claim 1 wherein the reaction time of nitration is effected in the range of 0.25 to 3.0 h.

7. A process as claimed in claim 1 wherein the product ratio for ortho:meta:para ranges from 29.4:2.3:65.7 to 5.4:6.5:36.4 depending upon the catalyst used.

8. A process as claimed in claim 1 wherein the product ratio for ortho:meta:para ranges from 13:0:87 to 25:0:73 depending upon the substrate used.

9. A process as claimed in claim 1 wherein selectivity of p-isomer increases to the extent of 5–10% with the increase of catalyst amount.

10. A process as claimed in claim 1 which is carried out in the absence of sulfuric acid.

11. A process as claimed in claim 1 wherein the catalyst not only imparts high activity by the presence of acidic sites but also high para selectivity due to the restricted dimensional configuration of the catalysts.

12. A process as claimed in claim 1 wherein the solid acid catalysts used here act as bifunctional catalysts, generating electrophile, nitronium ion as well as instant adsorbent for water formed during the reaction to facilitate electrophilic substitution on arenes.

13. A process as claimed in claim 1 wherein nitration is effected by continuous azeotropical removal of water present in the nitric acid and formed from the reaction mixture with Dean-Stark apparatus using substrate as self solvent or chlorhydrocarbons as solvent to regenerate active sites of the catalyst generating nitronium ions.

14. A process as claimed in claim 1 wherein recovery of nitroarenes is carried out by separating the catalyst by filtration and removing the excess aromatic hydrocarbons by distillation or by concentration in rotavapor.

* * * * *